United States Patent [19]

Westerberg et al.

[11] Patent Number: 5,144,984
[45] Date of Patent: Sep. 8, 1992

[54] ARRANGEMENT FOR FILLING AND TAPPING AN ANESTHETIC CONTAINER

[75] Inventors: Hans Westerberg, Tyresoe; Bill Thorsen, Bro, both of Sweden

[73] Assignee: Siemens Aktiengesellschaft, Munich, Fed. Rep. of Germany

[21] Appl. No.: 677,106

[22] Filed: Mar. 29, 1991

[30] Foreign Application Priority Data

Mar. 30, 1990 [SE] Sweden ............................. 9001173

[51] Int. Cl.⁵ .............................................. F16K 3/00
[52] U.S. Cl. ............................. 137/625.18; 137/616.7
[58] Field of Search ................... 137/625.18, 595, 616, 137/616.7

[56] References Cited

U.S. PATENT DOCUMENTS

| | | | |
|---|---|---|---|
| 2,664,084 | 12/1953 | Hammermann | 128/188 |
| 3,434,498 | 3/1969 | Eberhart | 137/625.18 |
| 3,469,603 | 9/1969 | Nagel | 137/616.7 X |
| 4,589,445 | 5/1986 | Sanchez Aguilar et al. | 137/616.7 |
| 4,662,396 | 5/1987 | Avnon | 137/616.7 |
| 4,662,400 | 5/1987 | Hecker | 137/625.18 |

FOREIGN PATENT DOCUMENTS 0295671  6/1988  European Pat. Off. .
1394216  5/1975  United Kingdom .

Primary Examiner—John Rivell
Attorney, Agent, or Firm—Hill, Van Santen, Steadman & Simpson

[57] ABSTRACT

A connector for facilitating transfer of anesthetic between an anesthetic gasifying apparatus and an anesthetic container. The connector includes a first articulated arm member associated with the anesthetic gasifying apparatus and including a pair of first fluid channels. A second articulated arm member, associated with the anesthetic container, is pivotably connected to the first articulated arm member, and includes a pair of second fluid channels. The first and second anesthetic channels may be brought into fluid communication with one another by pivoting the first and second arm members into predetermined relative angular positions.

4 Claims, 4 Drawing Sheets

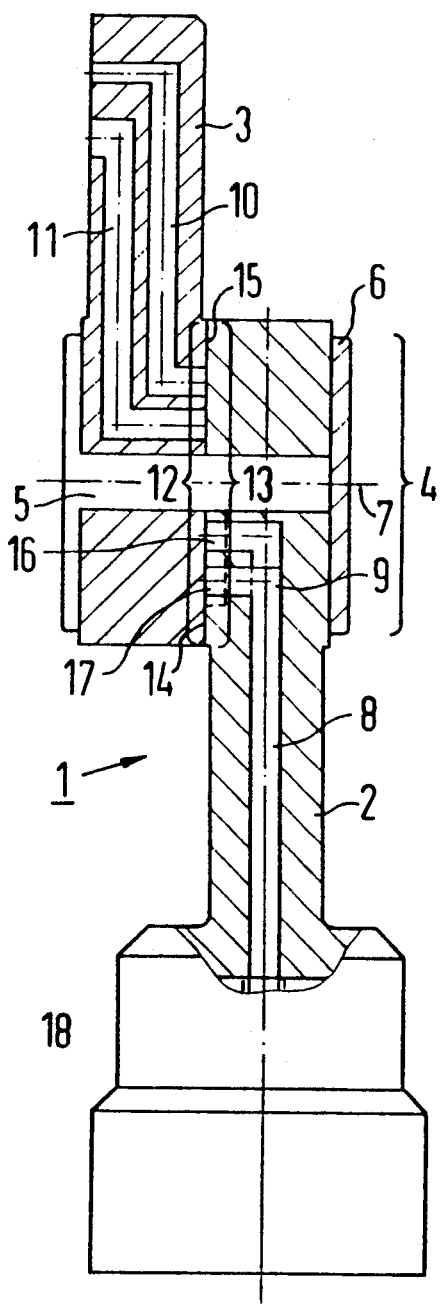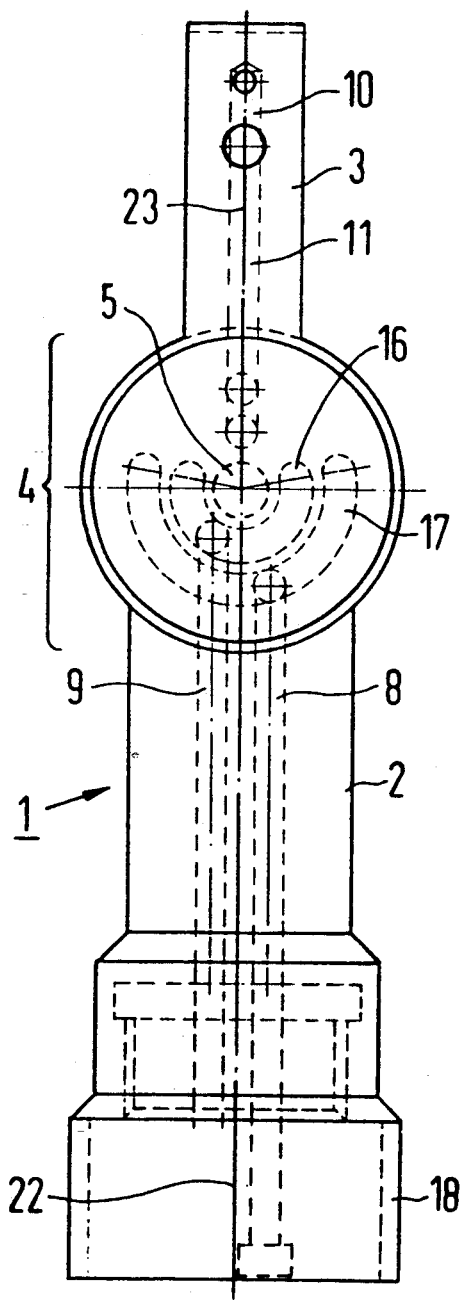

5,144,984

ARRANGEMENT FOR FILLING AND TAPPING AN ANESTHETIC CONTAINER

TECHNICAL FIELD

The present invention is directed to an arrangement for filling an anesthetic gasifying apparatus with anesthetic from a container, and for tapping (or decanting) anesthetic from the gasifying apparatus into the container. Specifically, the present invention is directed to a connector for facilitating transfer of anesthetic between a gasifying apparatus and a container.

BACKGROUND OF THE INVENTION

Various arrangements have been provided for transferring anesthetic between an anesthetic container and an anesthetic gasifying apparatus. One such anesthetic transfer arrangement is disclosed in British Patent No. 1 394 216. This arrangement includes a connector in the form of a plastic hose in which channels are formed. One end of the plastic hose is provided with a bottle stopper for connection with an anesthetic container. The other end of the hose is adapted for connection to an anesthetic gasifying apparatus. This arrangement has no valve or other mechanism for controlling the flow of anesthetic through the connector during anesthetic transfer and, due to the risk of anesthetic escape, cannot be used in operating rooms. Therefore, it is common practice with such known arrangements to fill or tap the anesthetic gasifying apparatus beneath a closed hood outside the operating room. Furthermore, the structural configuration of the known arrangements require the operator to constantly hold the anesthetic container in a particular position in order to control the flow of anesthetic.

SUMMARY OF THE INVENTION

It is, therefore, an object of the present invention to provide an arrangement for transferring anesthetic between an anesthetic gasifying apparatus and an anesthetic container that minimizes the risk of escape of anesthetic, and that is relatively easy to operate.

These and other objects of the invention are achieved by providing a connector for facilitating transfer of anesthetic between anesthetic gasifying apparatus and an anesthetic container that includes first and second articulated arm members. The first articulated arm member, which may be associated with the anesthetic gasifying apparatus, includes a pair of first fluid channels for conducting anesthetic and air, respectively. The second articulated arm member, which may be associated with the anesthetic container, is pivotably connected to the first articulated arm member, and includes a pair of second fluid channels. The first and second fluid channels may be brought into fluid communication with one another by pivoting the first and second arm members into predetermined relative angular positions.

Due to the structure of the connector part, the interface between the first and second articulated arm members acts as a value to open or close fluid communication between the first and second fluid channels when filling and emptying an anesthetic gasifying apparatus. The arrangement minimizes the escape of anesthetic.

In a preferred embodiment, a first seating surface is disposed at an interface portion of the first articulated arm, with each of the first fluid channels having a terminal opening disposed on the first seating surface. A second seating surface is disposed at an interface portion of the second articulated arm, and each of the second fluid channels have a terminal opening disposed on the second seating surface. The first and second arm members are pivotably secured together such that the first and second seating surfaces are maintained in substantially fluid tight engagement with one another.

A connecting groove arrangement may be provided in one of the interface portions, in order to provide selective fluid communication between the terminal openings of the respective pairs of fluid channels. In a preferred embodiment, the connecting groove arrangement includes a plurality of generally arcuate connecting grooves arranged concentrically about the pivot axis of the arm members.

The arm members are pivotable to an axially aligned position in which the grooves are incapable of providing fluid communication between the terminal openings of the respective pairs of fluid channels.

In this arrangement, the articulated arm members are brought into positively identifiable predetermined angular positions for either filling or tapping the anesthetic gasifying apparatus. The arm members are secured together so that they are retained in various angular positions, thus eliminating the need for the operator to hold the anesthetic container in a fixed position.

Other objects and advantages of the present invention will be apparent upon reference to the accompanying description when taken in conjunction with the following drawings.

BRIEF DESCRIPTION OF THE DRAWINGS

FIG. 1 illustrates a part-sectional view of a connector embodying the principles of the present invention.

FIG. 2 illustrates a front elevational view of the apparatus shown in FIG. 1.

DESCRIPTION OF THE PREFERRED EMBODIMENT

Figure 3:
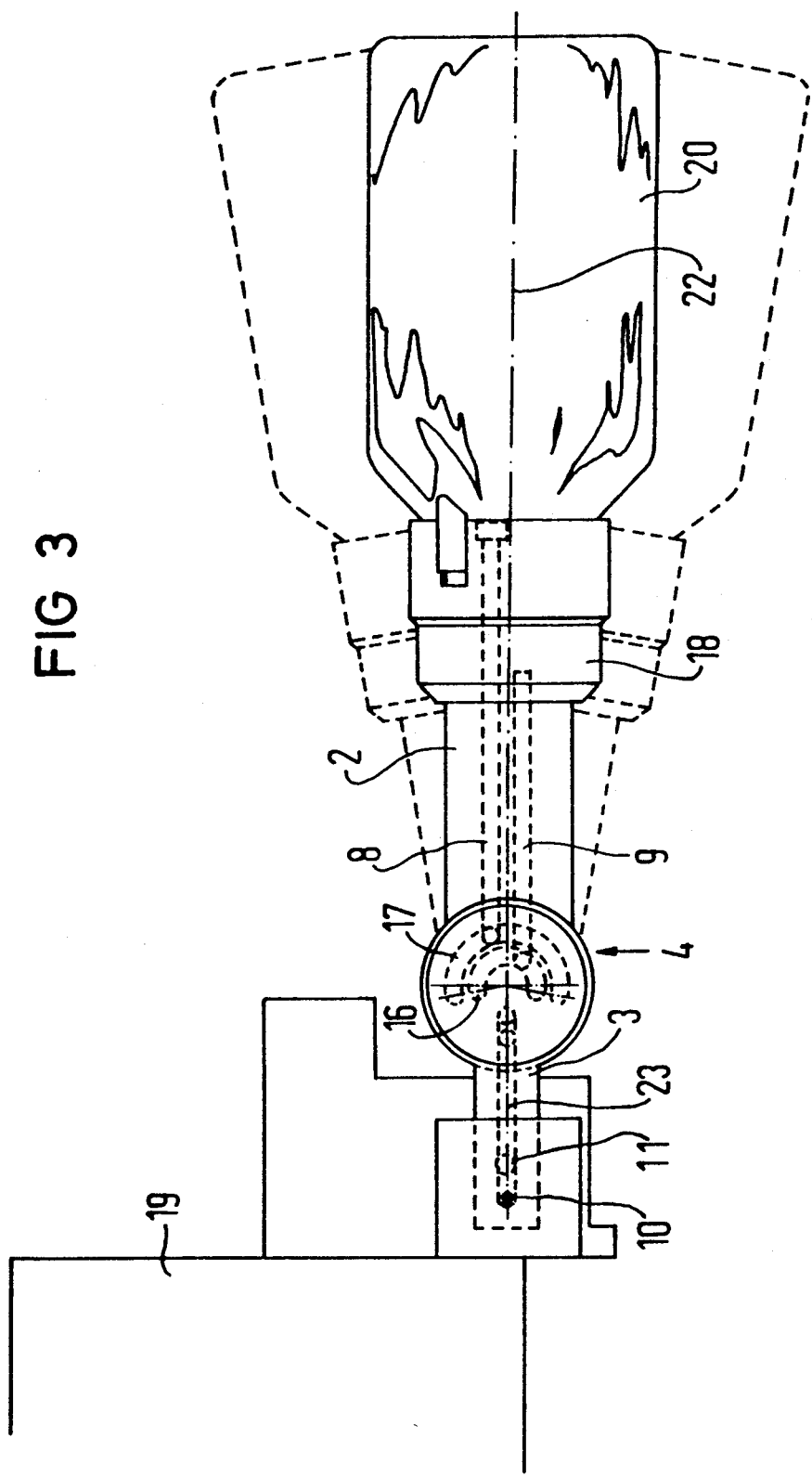
FIGS. 3 through 5 illustrate the connector of FIGS. 1 and 2, connected to an anesthetic gasifying apparatus and anesthetic container, in various operating positions.

FIG. 1 illustrates an apparatus embodying the principles of the present invention including a connector part 1 having a first articulated arm member 2 and a second articulated arm member 3. The articulated arm members are pivotably secured to one another with an articulation assembly 4. The assembly 4 includes a flanged shaft 5 and a nut 6. The longitudinal axis of the shaft 5 is concurrent with the center line 7 of the assembly 4, which forms the pivot axis of the connector 1. The articulation assembly 4 includes an interface portion 12 at one end of the articulated arm 3, and a second interface portion 13 at an end of the articulated arm 2. The interface portion 12 includes a seating surface 14, and the interface portion 13 includes a seating surface 15. The articulated arm 2 is provided with an air channel 8 and an anesthetic channel 9, with the channels 8 and 9 each having a terminal opening disposed on the seating surface 15. The articulated arm 3 is provided with an air channel 10 and an anesthetic channel 11, each of which has a terminal opening disposed on the seating surface 14.

The interface portion 12 is provided with a generally arcuate groove 16 in fluid communication with the channel 9, and a generally arcuate groove 17 in communication with the channel 8. The ends of the channels 8 and 9 opposite the grooves 16 and 17 discharge into a bottle stopper 18 connected to a free end of the articulated arm member 2.

As can be seen in FIG. 2, the grooves 16, 17 are concentrically arranged about the longitudinal axis 7 of the shaft 5. Furthermore, the grooves are configured such that the articulated arm members are pivotable to an axially aligned position in which the grooves 16, 17 block fluid communication between the terminal openings of the respective pairs of channels.

FIG. 3 illustrates the embodiments shown in FIGS. 1 and 2 during filling of an anesthetic gasifying apparatus. The bottle stopper 18 of the connector 1 is connected to an anesthetic container in the form of a bottle 20 filled with anesthetic. The free end of the articulated arm member 3 is connected so that the ends of the channels 10 and 11 discharge into an opening of the anesthetic gasifying apparatus 19. In FIG. 3, the connector 1 is shown in a position wherein the fluid connection between the bottle 20 and the anesthetic gasifying apparatus 19 is blocked. In this position, no anesthetic can escape. Even when the bottle 20 connected to the articulated arm member 2 is swivelled somewhat upwardly or downwardly relative to the horizontal plane (as indicated in broken line), fluid communication between the anesthetic gasifying apparatus 19 and the bottle 20 remains blocked.

Figure 4:
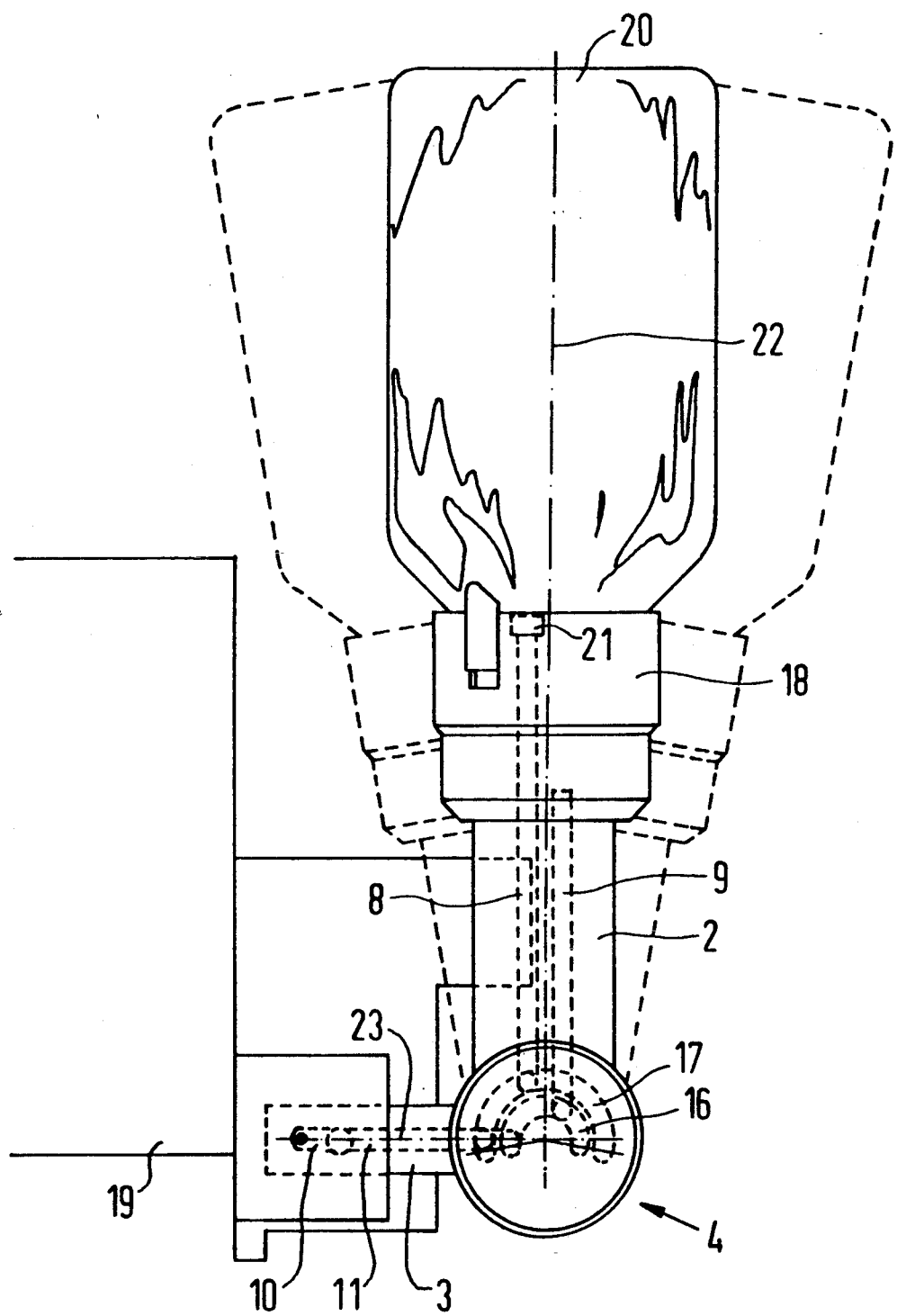

Use of the present invention during filling of the anesthetic gasifying apparatus 19 is shown in FIG. 4. During filling of the apparatus 19, the bottle 20 is pivoted into a vertical position, so that the opening of the bottle points downwardly. In this position, the grooves 16, 17 are disposed such that the openings of the channels 10, 11 of the articulated arm 3 overlie the grooves 16, 17, thus permitting fluid communication between the channels 8, 9 of the articulated arm member 2 and the channels 10, 11 of the articulated arm member 3. Anesthetic can flow from the bottle 20 through the channel 9 via the groove 16, and through the channel 11 to the anesthetic gasifying apparatus 19. The air channels 8 and 10, in conjunction with the groove 17, inhibit the formation of a partial vacuum from forming in the interior of the bottle 20. A check valve 21 may be provided at the free end of the air channel 8, in order to prevent anesthetic from entering into the air channel.

In the position shown in FIG. 4, the bottle 20 may be pivoted (as shown in broken line) without interrupting fluid communication between the channels of the articulated arm members.

Figure 5:
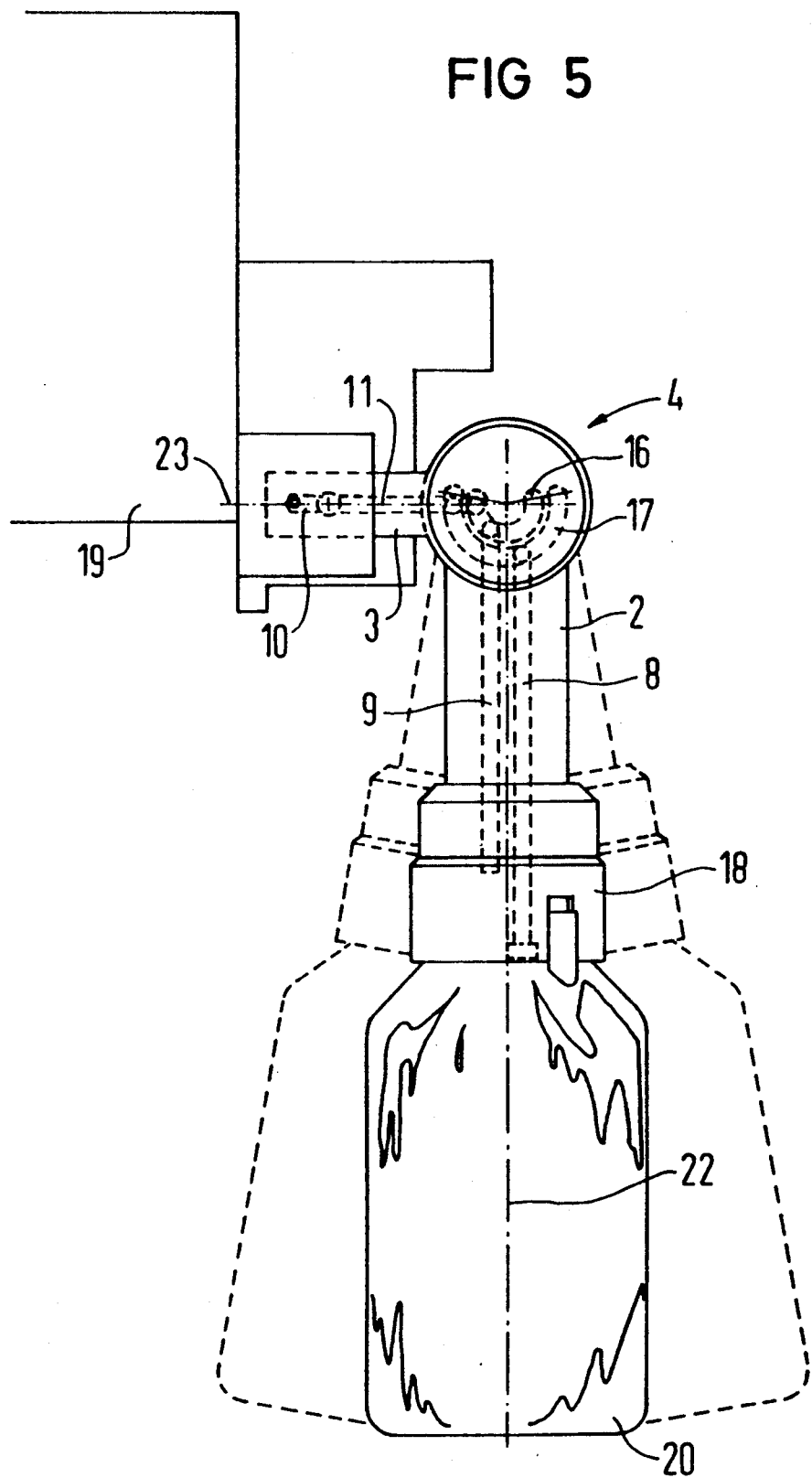

FIG. 5 shows the connector of FIGS. 1 and 2 employed in tapping or decanting anesthetic from the anesthetic gasifying apparatus 19. In the illustrated position, the bottle 20 at the end of the articulated arm member 2 is pivoted around the articulation assembly 4 into a vertical position, wherein the opening of the bottle 20 points upwardly. In this position, the articulated arm members are aligned so that the openings of the channels 10, 11 of the articulated arm member 3 overlie the grooves 16, 17, thus permitting fluid communication between the channels 8, 9 of the articulated arm member 2 and the channels 10, 11 of the articulated arm member 3. During decanting, anesthetic can flow from the anesthetic gasifying apparatus 19 through the channel 11 of the articulated arm 3 via the grooves 16, 17, through the channel 9 of the articulated arm member 2, and into the bottle 20. As with the positions shown in FIGS. 3 and 4, the bottle 20 can be pivoted to a limited degree without interrupting fluid communication between the gasifying apparatus 19 and the bottle 20 (as shown in broken line). As can be seen in FIGS. 4 and 5, the rotational angle between the filling position and the decanting position is approximately 180°.

The shaft 5 and the nut 6 of the articulation assembly 4 secure the articulated arm members together such that the interface portions 12, 13 press against one another. Thus, in addition to maintaining fluid-tight contact between the seating surfaces, contact between the interface portions is sufficient to retain the bottle 20 in various angular positions, thus eliminating the need for an operator to hold the bottle during anesthetic transfer.

It is to be understood that the foregoing embodiments are merely illustrative of the principles of the present invention. For example, it is contemplated that the grooves 16, 17 could be provided in either of the interface portions.

Although the present invention has been described with reference to a specific embodiment, those of skill in the art will recognize that changes may be made thereto without departing from the scope and spirit of the invention as set forth in the appended claims.

We claim as our invention:

1. A connector for facilitating transfer of anesthetic between an anesthetic gasifying apparatus and an anesthetic container, said connector comprising the following:

a first articulated arm member associated with said anesthetic gasifying apparatus and including a pair of first fluid channels;

a second articulated arm member, associated with said anesthetic container, pivotably connected to said first articulated arm member and including a pair of second fluid channels;

a first seating surface, disposed at an interface position of said first articulated arm, each of said first fluid channels having a terminal opening disposed on said first seating surface:

a second seating surface, disposed at an interface position of said second articulated arm, each of said second fluid channels having a terminal opening disposed on said second seating surface;

securing means for maintaining said first and second seating surfaces in substantially fluid-tight engagement with one another; and connecting groove means, in one of said interface positions, for providing selective fluid communication between the terminal openings of the respective pairs of fluid channels;

whereby said first and second pairs of channels may be brought into fluid communication with one another by pivoting said first and second arm members into predetermined relative angular positions including a filling position and a decanting position.

2. A connector according to claim 1, wherein said first and second arm members are pivotable about a predetermined axis, and said connecting groove means comprises a plurality of generally arcuate connecting grooves arranged concentrically about said axis.

3. A connecting according to claim 2, wherein said arm members are pivotable to an axially aligned position in which said grooves are incapable of providing fluid communication between the terminal openings of the respective pairs of fluid channels.

4. A connector according to claim 1, wherein a roational angle between said filling position and said decanting position is approximately 180°.

* * * * *